United States Patent [19]

Goldstein et al.

[11] 4,261,886
[45] Apr. 14, 1981

[54] PEPTIDES HAVING THYMOPOIETIN-LIKE ACTIVITY

[75] Inventors: Gideon Goldstein, Short Hills; George Heavner, Flemington, both of N.J.

[73] Assignee: Ortho Pharmaceutical Corporation, Raritan, N.J.

[21] Appl. No.: 124,959

[22] Filed: Mar. 13, 1980

Related U.S. Application Data

[63] Continuation-in-part of Ser. No. 29,595, Apr. 12, 1979.

[51] Int. Cl.$^3$ .......................................... C07C 103/52
[52] U.S. Cl. ........................................... 260/112.5 R
[58] Field of Search .................. 260/112.5 R; 424/177

[56] References Cited

U.S. PATENT DOCUMENTS 4,079,127 3/1978 Goldstein et al. ............ 260/112.5 R Primary Examiner—Delbert R. Phillips
Attorney, Agent, or Firm—Geoffrey G. Dellenbaugh

[57] ABSTRACT

There are disclosed peptides having the following formula:

$$\overset{1}{\underset{2}{\text{A-X-Z-Y-B}}}$$

wherein A is

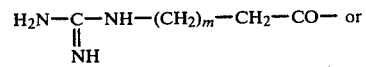

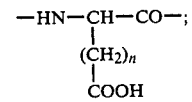

X is a suitable neutral, aliphatic or aromatic amino acid residue; e.g., one selected from the group consisting of ALA, 2-Me-ALA, GLY, LEU, ILE, LYS, THR, SER, PHE, MET, D-ALA, D-LEU, D-ILE, D-LYS, D-THR, allo-THR, D-SER, D-PHE, D-MET, and SAR; Z is $$-\text{HN}-\overset{|}{\underset{\underset{\text{COOH}}{(\text{CH}_2)_n}}{\text{CH}}}-\text{CO}-;$$

Y is GLY, SER, THR, LEU, ILE, VAl, or SAR; B is TYR-R', D-TYR-R', decarboxy-TYR, or

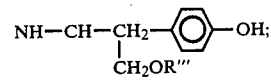

m is 3 or 4; n is 1, 2, or 3; R''' is hydrogen, $C_1$–$C_7$ alkyl, $C_6$–$C_{12}$ aryl, or $C_1$–$C_7$ alkanoyl; and R and R' are substituents which do not substantially affect the biological activity of the peptides, provided that R-ARG-LYS-ASP-VAL-TYR-R' is excluded. These peptides have the capability of inducing the differentiation of T-lymphocytes but not of complement receptor (CR+) B-lymphocytes and thus are useful in a number of therapeutic areas. Also provided are derivatives of the peptides, therapeutic compositions, and methods for use of the compositions.

33 Claims, No Drawings

PEPTIDES HAVING THYMOPOIETIN-LIKE ACTIVITY

REFERENCE TO RELATED APPLICATION

This application is a continuation-in-part of our co-pening application Ser. No. 29,595, filed Apr. 12, 1979.

BACKGROUND OF THE INVENTION

1. Field of the Invention

This invention relates generally to new peptides and their derivatives, therapeutic compositions containing the same, and methods for use of the compositions.

2. Description of the Prior Art

U.S. Pat. No. 4,190,646, of which one of the present Applicants is one of the named inventors, discloses the pentapeptide of sequence H-ARG-LYS-ASP-VAL-TYR-OH as well as peptide compositions in which various groups are substituted onto the amino- or carboxyl-terminus of this pentapeptide. This patent is incorporated herein by reference. For brevity herein, the pentapeptide, the sequence of which is given above, will be referred to as the "thymopoietin pentapeptide" or "TP5". The above-referenced patent discloses that the thymopoietin pentapeptide and its derivatives have biological activity similar to that of the long chain polypeptide known as thymopoietin and described in U.S. Pat. Nos. 4,002,740 and 4,077,949. The thymopoietin pentapeptide, which was disclosed to be the most active compound set out in the patent, showed activity in the mouse assay of Example II thereof at concentrations ranging from 1 ng/ml to 10 μg/ml. The biological activity of TP5 is also disclosed in an article by M. E. Weksler, et al., *J. Exp. Med.* 148:996-1006 (1978). This article is incorporated herein by reference.

Reference is made to the above-described thymopoietin pentapeptide patent and article for a discussion of other prior art and the biological processes involved in the present invention.

The present invention provides peptides and peptide compositions which are surprisingly and significantly more active than the thymopoietin pentapeptide.

SUMMARY OF THE INVENTION

It is therefore one object of this invention to provide new peptides and their derivatives which have the ability to induce differentiation of bone marrow cells to T cells, thus giving rise to thymus-derived lymphocytes and which are therefore highly useful in the immune system of humans and animals.

A further object is to provide peptides which have this differentiating ability in picogram/ml concentrations.

A still further object is to provide compositions containing these peptides and derivatives and methods for use in therapeutic action.

Other objects and advantages of the invention will become apparent as the description proceeds.

In satisfaction of the foregoing objects and advantages there is provided by this invention the novel pentapeptides having the following sequence:

A-X-Z-Y-B

I.

wherein A is

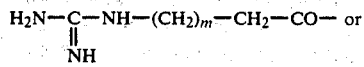

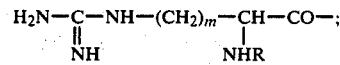

X is a suitable neutral, aliphatic or aromatic amino acid residue; e.g., one selected from the group consisting of ALA, 2-Me-ALA, GLY, LEU, ILE, LYS, THR, SER, PHE, MET, D-ALA, D-LEU, D-ILE, D-LYS, D-THR, allo-THR, D-SER, D-PHE, D-MET, and SAR; Z is

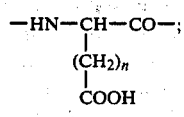

Y is GLY, SER, THR, LEU, ILE, VAL, or SAR; B is TYR-R', D-TYR-R', decarboxy-TYR, or

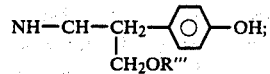

m is 3 or 4; n is 1, 2, or 3; R''' is hydrogen, $C_1$-$C_7$ alkyl, $C_6$-$C_{12}$ aryl, or $C_1$-$C_7$ alkanoyl; and R and R' are substituents which do not substantially affect the biological activity of the peptides, provided that R-ARG-LYS-ASP-VAL-TYR-R' is excluded.

Also provided are derivatives of these novel pentapeptides, as well as therapeutic compositions containing either the pentapeptides of their derivatives, and methods for administration of either the pentapeptides or their derivatives to humans and animals for affecting biological actions thereon.

It has surprisingly been found that the subject peptides are as much as 10,000 times more potent than the thymopoietin pentapeptide. Since it is not generally possible in the polypeptide art to predict the effect of substitutions in the active region of a polypeptide, it is by no means obvious that the subject compounds would possess any activity at all, let alone the striking potency found. This unpredictable nature is demonstrated by the fact that the pentapeptide H-ARG-SAR-ASP-SAR-TYR-NH$_2$ (SAR$^2$, SAR$^4$-TP5 amide) claimed herein was found to be active at 0.1 pg/ml, in the assay of Example II, below.

DETAILED DESCRIPTION OF THE INVENTION

As indicated above, this invention is concerned with new peptides having therapeutic value in various areas, therapeutic compositions containing these peptides, and methods for use thereof.

In its broadest scope, the present invention provides peptides having the following formula:

A-X-Z-Y-B

I.

wherein A, X, Z, Y, and B are as defined above and R and R' are substituents which do not substantially affect the biological activity of the peptides. By this statement is meant that the terminal amino acids on this pentapeptide may be modified without departing from the scope of the invention by placing the functional groups or derivatives (R and R') on these terminal amino acids which do not substantially affect the biological activity of the molecule. Thus, it is to be understood that the terminal amino and carboxylic acid groups are not essential to the biological activity of the pentapeptides as is the case in some polypeptides. Therefore, it is considered that the scope of the present invention is inclusive of unsubstituted pentapeptides (those wherein R and R″=H and R'=OH) as well as those which are terminally substituted by one or more functional groups which do not substantially affect the biological activity disclosed herein.

From this statement it will be understood that these functional groups include such normal substitution as acylation on the free amino group and amidation on the free carboxylic acid group, as well as the substitution of additional amino acids and peptides. The pentapeptides of this invention appear to be highly unusual since they exhibit the same biological activity as the long chain natural peptide thymopoietin, a portion of which the subject pentapeptides resemble. It is believed therefore that the activity requirements of the molecule are generated by stereochemistry of the molecule, that is, the particular "folding" of the molecule. In this regard, it should be understood that polypeptide bonds are not rigid but flexible, thus allowing polypeptides to exist as sheets, helices, and the like. As a result, the entire molecule is flexible and will "fold" in a certain way. In the present invention it has been discovered that the pentapeptide "folds" in the same manner as long chain natural polypeptide and therefore exhibits the same biological characteristics. For this reason, the pentapeptide may be substituted by various functional groups so long as the substituents do not substantially affect the biological activity or interfere with the natural "folds" of the molecule.

The ability of the pentapeptide to retain its biological activity and natural folding is illustrated by the fact that it has the same activity as disclosed for the thymopoietin pentapeptide in the above-referenced patent, as well as thymopoietin itself.

In view of this discussion, therefore, it will be understood that R and R' in Formula (I) can be any substituent that does not substantially affect the biological activity of the basic active sequence. Thus, for purposes of illustration, R and R' may be any of the following substituents:

| R | R' |
|---|---|
| Hydrogen | OH |
| $C_1$–$C_7$ alkyl | $NH_2$ |
| $C_6$–$C_{12}$ aryl | NHR″ |
| $C_6$–$C_{20}$ alkaryl | N(R″)$_2$ |
| $C_6$–$C_{20}$ aralkyl | OR″ |
| $C_1$–$C_7$ alkanoyl | |
| $C_2$–$C_7$ alkenyl | |
| $C_2$–$C_7$ alkynyl | | wherein R″ is $C_1$–$C_7$ alkyl, $C_2$–$C_7$ alkenyl, $C_2$–$C_7$ alkynyl, $C_6$–$C_{12}$ aryl, $C_6$–$C_{20}$ alkaryl, or $C_6$–$C_{20}$ aralkyl.

As pointed out above however, R and R' can also be neutral amino acid groups or residues of polypeptide chains having 1 to 20 carbon atoms. The following are illustrative:

| R | R' |
|---|---|
| GLN | VAL |
| GLU | GLN |
| GLY | LEU |
| GLU-GLN | TYR |
| GLY-GLN | VAL-GLN |
| GLY-GLU | VAL-LEU |
| GLY-GLU-GLN | VAL-TYR |
| | GLN-LEU |
| | GLN-TYR |
| | GLN-VAL |
| | LEU-TYR |
| | LEU-LEU |
| | TYR-LEU |
| | VAL-GLN-LEU |
| | VAL-GLN-LEU-TYR |
| | VAL-GLN-LEU-TYR-LEU |

Preferred compounds of formula I are those wherein m is 3 and n is 1 or 2; more preferred are those where m is 3 and n is 1.

In one more specific embodiment of the invention, there are provided novel peptides having the following formula:

A-X-Z-Y-B                    II.

wherein A is deamino ARG or R-ARG, X is selected from the group consisting of ALA, 2-Me-ALA, GLY, LEU, ILE, THR, SER, D-ALA, D-LEU, D-ILE, D-THR, allo-THR, D-SER, D-LYS, and SAR; Z is ASP or GLU; Y is VAL or SAR; and B is decarboxy TYR, TYR-R', or

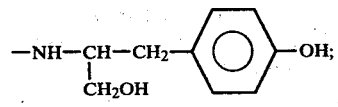

and R and R' are as previously defined. Preferred compounds within this embodiment are those wherein Z is ASP.

In another more specific embodiment of the invention, there is provided novel peptides having the following formula:

A-SAR-ASP-Y-B                III.

wherein Y is VAL or SAR, A is deamino-ARG or H-ARG; B is decarboxy-TYR, TYR-R', or

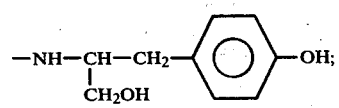

and R' is H, OH, or $NH_2$. More preferred peptides are those of Formula III wherein Y is SAR. Still more preferred peptides are those of Formula III wherein Y is SAR, B is TYR-R', and R' is $NH_2$.

Also included within the scope of the invention are the pharmaceutically acceptable salts of the peptides.

As acids which are able to form salts with the peptides, there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid or sulfanilic acid, for instance.

In the above structures the amino acid components of the peptides are identified as abbreviations for convenience. These abbreviations are as follows:

| Amino Acid | Abbreviated Designation |
|---|---|
| Glycine | GLY |
| L-alanine | ALA |
| L-glutamic acid | GLU |
| L-glutamine | GLN |
| L-arginine | ARG |
| L-lysine | LYS |
| L-aspartic acid | ASP |
| L-valine | VAL |
| L-threonine | THR |
| L-tyrosine | TYR |
| L-leucine | LEU |
| L-isoleucine | ILE |
| L-phenylalanine | PHE |
| L-methionine | MET |
| L-serine | SER |
| Sarcosine | SAR |
| D-alanine | D-ALA |
| D-leucine | D-LEU |
| D-isoleucine | D-ILE |
| D-threonine | D-THR |
| allo-threonine | allo-THR |
| D-serine | D-SER |
| D-phenylalanine | D-PHE |
| D-methionine | D-MET |
| D-tyrosine | D-TYR |
| D-lysine | D-LYS |
| 2-methylalanine | 2-Me-ALA |

The terms deamino-ARG and decarboxy-TYR as used herein refer, respectively, to an L-arginine moiety which has had its α-amino group replaced by hydrogen

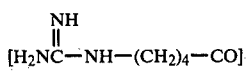

and an L-tyrosine moiety which has had its carboxy group replaced by hydrogen

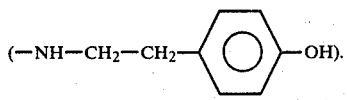

The definitions for A, B, and Z given above are intended to include both the D- and L-forms although the L-form is preferred. Thus, the ARG, TYR, and ASP analogs correspond in configuration to the model amino acid residues (D or L but preferably L) where these analogs are optically active. This will be the case for all except the deamino-ARG and decarboxy-TYR and analogs, which are not optically active.

The peptides of this invention have been found to exhibit characteristics similar to the 49-amino acid polypeptide isolated from bovine thymus (thymopoietin) disclosed in the above referenced United States patents. The peptides of this invention are particularly characterized in their ability to induce the selective differentiation of Thy-1+ T cells (but not CR+ B cells), in concentrations of 0.1 pg/ml to 10 ng/ml. Thy-1 is a differentiation alloantigen present on T cells but not B cells whereas CR is a complement receptor present on B cells but not T cells.

Studies of these synthetic peptides in the induction assay in vitro showed them to have the same induction specificity as Thymopoietin II. That is, they induced the differentiation of Thy-1− cells of Thy-1+ T cells, but did not induce the differentiation of CR− cells to CR+ B cells. While many substances have been identified that can mimic thymopoietin in vitro and induce T cell differentiation by raising intracellular cyclic AMP, it is emphasized that few substances are active at such low concentration, and the peptides of this invention are selective in inducing T cell differentiation but not CR+ B cell differentiation.

Because of these characteristics of the peptides of this invention, they are therapeutically useful in the treatment of humans and animals since they have the capability for inducing the differentiation of lymphopoietic stem cells originating in the haemopoietic tissues to thymus-derived cells or T cells which are capable of involvement in the imume response to the body. As a result, the product of this invention are considered to have multiple therapeutic uses. Primarily, since the compounds have the capability of carrying out certain of the indicated functions of the thymus, they have appalication in variou thymic function and immunity areas. A primary field of application is in the treatment of DiGeorge Syndrome, a condition in which there is a congenital absence of thymus. Injection of the peptides will overcome this deficiency. Because of their biological characteristics, which are extremely active at low concentrations, they are considered useful in assisting the collective immunity of the body in that the peptides will increase or assist in therapeutic stimulation of cellular immunity and thereby become useful in the treatment of diseases involving chronic infection in vivo, such as fungal or mycoplasma infections, tuberculosis, leprosy, acute and chronic viral infections, and the like. Further, the compounds are considered to be useful in any area in which cellular immunity is an issue and particularly where there are deficiencies in immunity such as in the DiGeorge Syndrome mentioned above. Also, where there is an excess of antibody production due to unbalanced T cells and B cells, the compounds can correct this condition by stimulating T cell production. Thys, they may be of therapeutic use in certain autoimmune diseases in which damaging antibodies are present, for example, systemic lupus erythematosus. Further, because of the characteristics of the peptides, they have in vitro usefulness in inducing the development of surface antigens of T cells, in inducing the development of the functional capacity to achieve responsiveness to mitogens and antigens and cell collaborativity in enhancing the ability of B cells to produce antibodies. The peptides are also useful in inhibiting the uncontrolled proliferation of thymopoietin-responsive lymphocytes.

An important characteristic of the peptides is their in vivo ability to restore cells with the characteristic of T cells. Therefore, the peptides of this invention are active in many areas as a result of their ability to enhance the immune response in the body. Since the peptides of this invention affect neuromuscular transmission, very high doses of the peptides of this invention will be useful in treating diseases with excess neuromuscular transmission, such as spasticity.

A further important property of the peptides of this invention is that they are highly active in very low concentrations ranging from 0.1 pg/ml. The carrier may be any of the well-known carriers for this purpose including normal saline solutions, preferably with a protein diluent such as bovine serum albumin (BSA) to prevent adsorptive losses to glassware at these low concentrations. The peptides of this invention are active parenterally at about 1 ng/kg of body weight. For the treatment of DiGeorge Syndrome, the polypeptides may be administered at a rate of about 0.1 to 10 ng/kg of body weight. Generally, the same range of dosage amounts may be used in treatment of the other conditions or diseases mentioned.

To prepare the pharmaceutical compositions of the present invention, polypeptide of Formula (I) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The parenteral pharmaceutical compositions of the invention should be designed to administer the subject polypeptides at a rate of about 0.1 to about 100 ng/kg of body weight. The oral compositions should administer about 100 to 1000 times the dose for parenteral administration—i.e., from about 10 ng/kg to about 100 µg/kg of body weight. Accordingly, the parenteral compositions should contain, per dosage unit, from about 5 ng to about 5 µg, whereas the oral compositions should contain, per dosage unit, from about 500 ng to about 5 mg of the subject polypeptide.

The polypeptides of this invention were prepared using concepts similar to the method of Merrifield as reported in *Journal of American Chemical Society*, 85, pp 2149–2154, 1963. The synthesis involved the stepwise addition of protected amino acids to a growing peptide chain which was bound by covalent bonds to a solid resin particle. By this procedure, reagents and by-products were removed by filtration and the recrystallization of intermediates as eliminated. The general concept of this method depends on attachment of the C-terminal amino acid of the chain to a solid polymer by a covalent bond and the addition of the succeeding amino acids one at a time in a stepwise manner until the desired sequence is assembled. Finally, the peptide is removed from the solid support and protecting groups removed. This method provides a growing peptide chain attached to a completely insoluble solid particle so that it is in a convenient form to be filtered and washed free of reagents and by-products.

The amino acids may be attached to any suitable polymer which merely has to be readily separable from the unreacted reagents. The polymer may be insoluble in the solvents used or may be soluble in certain solvents and insoluble in others. The polymer should have a stable physical form permitting ready filtration. It must contain a functional group to which the first protected amino acid can be firmly linked by a covalent bond. Various insoluble polymers suitable for this purpose are those such as cellulose, polyvinyl alcohol, polymethacrylate and sulfonated polystyrene but in the synthesis of this invention, there was used a chloromethylated copolymer of styrene and divinylbenzene. Polymers which are soluble in organic solvents while being insoluble in aqueous solvents may also be used. One such polymer is a polyethylene glycol having a molecular weight of about 20,000, which is soluble in methylene chloride but insoluble in water. The use of this polymer in peptide synthesis is described in F. Bayer and M. Mutter, *Nature* 237, 512 (1972) and references contained therein.

The various functional groups on the amino acid which were active, but which were not to enter into the reactions, were protected by conventional protecting groups as used in the polypeptide art throughout the reaction. Thus, the functional group on lysine was protected by protecting groups which could be removed on completion of the sequence without adversely affecting the polypeptide final product. In the synthesis ninhydrin was used to determine if coupling was complete. If complete coupling was not indicated, the coupling was repeated with the same protected amino acid before deprotection.

The C-terminal amino acid may be attached to the polymer in a variety of well-known ways. Summaries of methods for attachment to halomethyl resins are given in Horiki, et. al., *Chem. Letters*, pp 165–168 (1978) and Gisin, *Helv. Chim. Acta*, 56, 1476 (1973), and references given therein. If a C-terminal amide is to be prepared, one of two routes may be employed. Either the peptide resin prepared according to the Merrifield technique may be cleaved from the resin using anhydrous ammonia, or a benzhydrylamine resin may be employed. Cleavage from this latter resin with hydrogen fluoride affords the C-terminal amide peptide. The use of a benzhydrylamine resin is shown in, for example, J. Rivier, et al., *J. Med. Chem.*, 16, pp 545–549 (1973).

The general procedure for preparation of C-terminal carboxyl peptides involved initially esterifying L-tyrosine, protected on its amino and hydroxyl groups, to the chloromethyl resin by the $CsHCO_3$ method of Gisin. The protecting group on the $\alpha$-amino group of the tyrosine amino acid (e.g., t-BOC, i.e., t-butyloxycarbonyl), was then removed without affecting other protecting groups. The coupled amino acid resin was then filtered, washed, and neutralized. The resulting coupled amino acid-resin, having the free amino group, was then reacted with a protected L-valine, preferably alpha t-BOC-L-valine to couple the L-valine to the amino acid-resin. The reactions were then repeated with protected L-aspartic acid, sarcosine and L-arginine until the complete molecule was prepared. This procedure was used in formation of the basic five-amino acid active sequence. The addition of other neutral amino acid residues on either end of the chain is carried out using the same sequence of reactions as known in the art. The sequence of reactions to prepare the five member amino acid active site may be carried out as follows:

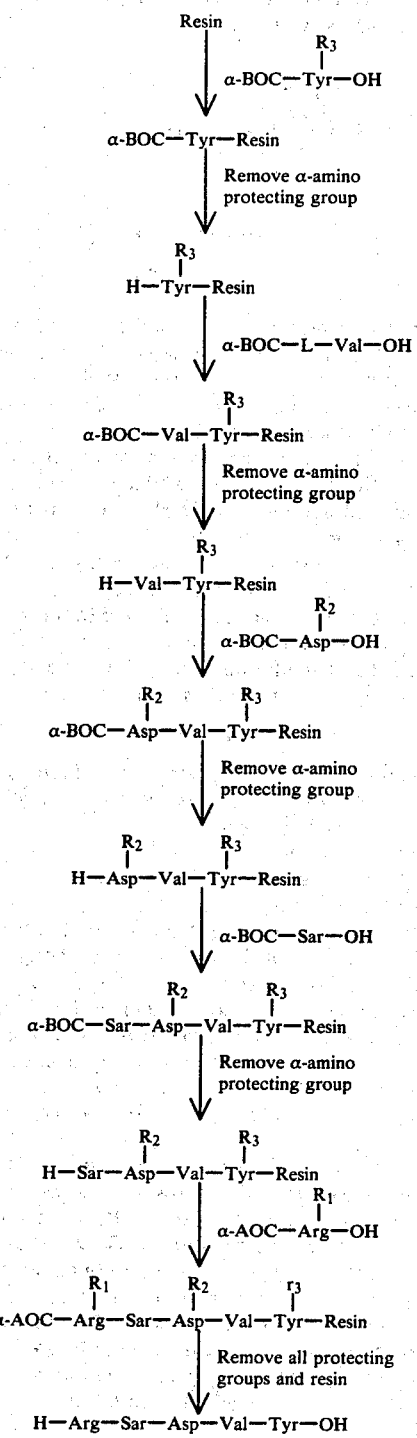

In the above sequence of reactions $R_1$, $R_2$, and $R_3$ are protecting groups on the various reactive groups on the amino acid side chains which are not affected or removed when the α-amino protecting group is removed to permit further reaction. Preferably, in the above intermediate pentapeptide resin, the expression $R_1$ is tosyl (Tos), $R_2$ stands for benzyl (Bzl), and $R_3$ stands for bromobenzyloxycarbonyl. The resin is any of the resins mentioned above as being useful in the process to produce a C-terminal carboxyl peptide.

The peptide-resin is cleaved to free the peptide from the resin and protecting groups $R_1$, $R_2$, $R_3$, and t-AOC simultaneously to provide the final product peptide. The protecting groups and resin were cleaved by conventional means, e.g., by treatment with anhydrous hydrogen fluoride and the peptide recovered.

As pointed out above, in conducting the process it is necessary to protect or block the amino groups in order to control the reaction and obtain the products desired. Suitable amino-protecting groups which may be usefully employed include salt formation for protecting strongly-basic amino groups, or urethane protecting substituents such as benzyloxycarbonyl and t-butyloxycarbonyl. It is preferred to utilize t-butyloxycarbonyl (t-BOC) or t-amyloxycarbonyl (t-AOC) for protecting the α-amino group in the amino acids undergoing reaction at the carboxyl end of the molecule, since the BOC and AOC protecting groups are readily removed following such reaction, and prior to the subsequent step (wherein such α-amino group itself undergoes reaction), by relatively mild action of acids (e.g., trifluoroacetic acid). This treatment does not otherwise affect protecting groups on said chains. It will thus be understood that the α-amino group may be protected by reaction with any material which will protect the α-amino group for the subsequent reaction(s) but which may later be removed under conditions which will not otherwise affect the molecule. Illustrative of such materials are organic carboxylic or carbonic acid derivatives which will acylate the amino group.

In general, the amino groups can be protected by reaction with a compound containing a grouping of the formula:

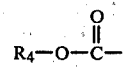

wherein $R_4$ is any grouping which will prevent the amino group from entering into subsequent coupling reactions and which can be removed without destruction of the molecule. Thus, $R_4$ is a straight or branched chain alkyl which may be unsaturated, preferably of 1 to 10 carbon atoms and preferably halo- or cyano-substituted; aryl, preferably of 6 to 15 carbons; cycloalkyl, preferably of 5 to 8 carbon atoms; aralkyl, preferably of 7 to 18 carbon atoms; alkaryl, preferably of 7 to 18 carbon atoms; or heterocyclic, e.g., isonicotinyl. The aryl, aralkyl, and alkaryl moieties may also be further substituted as by one or more alkyl groups of 1 to about 4 carbon atoms. Preferred groupings for $R_4$ include t-butyl, t-amyl, tolyl, xylyl, and benzyl. Highly preferred specific amino-protecting groups include benzyloxycarbonyl; substituted benzyloxycarbonyl wherein the phenyl ring is substituted by one or more halogens, e.g., Cl or Br, nitro, loweralkoxy, e.g., methoxy, or loweralkyl; t-butyloxycarbonyl; t-amyloxycarbonyl; cyclohexyloxycarbonyl; vinyloxycarbonyl; adamantyloxycarbonyl; biphenylisopropoxycarbonyl; and the like. Other protecting groups which can be used include isonicotinyloxycarbonyl, phthaloyl, p-tolysulfonyl, formyl and the like.

In conducting the general process of the invention, the peptide is built by reaction of the free α-amino group with a compound containing a blocked α-amino group. For reaction or coupling, the carboxyl component of the compound being attached is activated at its carboxyl group so that the carboxyl group can then react with the free α-amino group on the peptide chain. To achieve activation, the carboxyl group can be converted to any reactive group such as an ester, anhydride, azide, acid chloride, or the like. Alternately, a suitable coupling reagent may be added during the reaction. Suitable coupling reagents are disclosed, e.g., Bodanszky, et al., *Peptide Synthesis,* Interscience, second edition, 1976, chapter five, including carbodiimides (e.g., dicyclohexylcarbodiimide), carbonyldiimidazole, and the like.

It should also be understood that during these reactions, the amino acid moieties contain both amino groups and carboxyl groups and usually one grouping enters into the reaction while the other is protected. Prior to the coupling step, the protecting group on the alpha- or terminal-amino group of the peptide attached to the resin is removed under conditions which will not substantially affect other protecting groups, e.g., the group on the hydroxy group of the tyrosine molecule. The preferred procedure for effecting this step is mild acid hydrolysis, as by reaction at room temperature with trifluoroacetic acid.

As may be appreciated, the above-described series of process steps results in the production of the specific pentapeptide of the following formula:

H-ARG-SAR-ASP-VAL-TYR-OH      IV.

The substituted pentapeptides of Formula I, wherein the terminal ARG and TYR amino acid groups may be further substituted as described above, are then prepared by reaction of this pentapeptide or the protected peptide resin with suitable reagents to prepare the desired derivatives. Reactions of this type such as acylation, esterification, amidation and the like, are of course well-known in the art. Further, other amino acids, that is amino acid groups which do not affect the biological activity of the basic pentapeptide molecule, may be added to the peptide chain by the same sequence of reactions by which the pentapeptide was synthesized.

The corresponding C-terminal amide peptides may be prepared as described above but substituting a benzhydrylamine resin for the chloromethyl resin used therein and coupling the C-terminal amino acid thereto by a suitable coupling agent such as dicyclohexylcarbodiimide.

The corresponding peptides of Formula I wherein A is deamino-ARG may be prepared by substituting an equivalent amount of suitably protected deamino-arginine for protected L-arginine in the above synthetic scheme.

The corresponding peptides of Formula I wherein B is decarboxy-TYR or

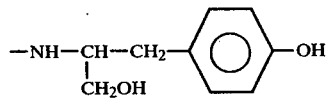

may be prepared following the procedure of T. W. Kirby and P. K. Warme, *Analytical Biochemistry,* 85, 367(1978). In this procedure a mercaptophenol resin is employed, to which is attached the penultimate suitably protected amino acid via its carboxyl group (i.e., α-BOC-L-Val-OH in synthesis of compound IV). The remainder of the blocked peptide is synthesized as described above, after which the bonding sulfur group on the resin is oxidized with m-chloroperbenzoic acid to yield an active ester resin. Treatment of this active ester resin with an equivalent amount of a suitably protected amino acid derivative (e.g.,

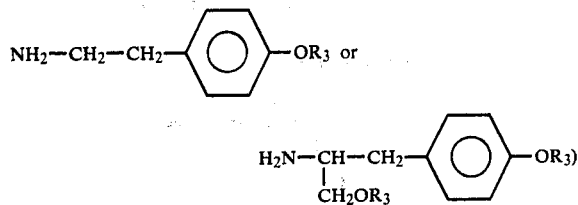

couples this derivative to the penultimate amino acid residue by simultaneous displacement of the peptide from the resin. Finally, the resulting blocked pentapeptide is treated with, e.g., anhydrous hydrogen fluoride to remove all protecting groups.

While the subject polypeptides were actually synthesized using the Merrifield solid-phase synthesis technique descrbied above, it is clearly contemplated that classical solution synthesis techniques may be employed. See, for example, M. Bodanszky and M. A. Ondetti, *Peptide Synthesis,* Interscience, 1966.

The following examples are presented to illustrate the invention but it is not to be considered as limited thereto. In the examples and throughout the specification, parts are by weight unless otherwise indicated.

EXAMPLE I

In preparation of one peptide of this invention the following materials were purchased commercially.
Alpha-AOC-N-Tos-L-arginine
Alpha-BOC-sarcosine
Alpha-BOC-O-benzyl-L-aspartic acid
Alpha-BOC-L-valine
Alpha-BOC-O-bromobenzyloxycarbonyl-L-tyrosine In these reagents, BOC is t-butyloxycarbonyl, AOC is t-amyloxycarbonyl, and Tos is tosyl. "Sequenal" grade reagents for amino acid sequence determination, dicyclohexylcarbodiimide, ninhydrin, and the resin were purchased commercially. The resin used was a polystyrene divinyl benzene resin, 200–400 mesh size containing 1% divinyl benzene and 0.75 mM of chloride per gram of resin.

In preparation of the pentapeptide, α-BOC-O-bromobenzyloxycarbonyl-L-tyrosine was esterified to chloromethylated resin by the $CsHCO_3$ method referred to in the above-referenced Gisin article. The resulting protected amino acid resin contained 0.4–0.5 mmole of amino acid per gram of resin. Using a Schwarz/Mann Automatic Peptide Synthesizer, the following program was used to couple each BOC-protected amino acid to the BOC-amino acid resin:

1. Prewashing with 40% TFA in $CH_2Cl_2$, once, 1.5 min.
2. Deprotection with 40% TFA in $CH_2Cl_2$, once, 20 min.
3. Washing with $CHCl_3$, once, 1.5 min.
4. Washing with EtOH, once, 1.5 min.
5. Washing with $CH_2Cl_2$, twice, 1.5 min.
6. Prewashing with 10% $Et_3N$ in $CH_2Cl_2$, once, 1.5 min.
7. Neutralization with 10% $Et_3N$ in $CH_2Cl_2$, once, 10 min.

8. Washing with CH$_2$Cl$_2$, three times, 1.5 min.
9. Addition of BOC-protected amino acid (5 molar excess) in DMF and CH$_2$Cl$_2$ (1:9 vol/vol).
10. Addition of DCC in CH$_2$Cl$_2$ (0.5 M 5 molar excess), the reaction time was up to 2 hours.
11. Washing with CH$_2$Cl$_2$, twice, 1.5 min.

Thereafter, the α-BOC or α-AOC amino acids were similarly coupled to the deprotected α-amino group of the peptide-resin in the correct sequence to result in one peptide of this invention using equivalent amounts of dicyclohexylcarbodiimide. After each coupling reaction, an aliquot of resin was tested with ninhydrin and if a positive result was found, coupling was taken to be incomplete and was repeated with the same protected amino acid. As the result of the several coupling reactions, the following pentapeptide-resin resulted:

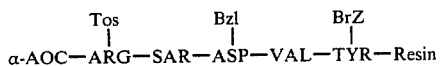

where AOC is amyloxycarbonyl, Tos is tosyl, Bzl is benzyl, and BrZ is bromobenzyloxycarbonyl.

This peptide-resin was cleaved and the protecting groups removed in a Kel-F cleavage apparatus (Peninsula Laboratories, Inc.) using 10 ml anhydrous hydrogen fluoride per gram of resin at 0° C. for 60 minutes with 5 ml anisole per gram peptide-resin as scavenger. After evaporation in vacuo to dryness, the residue was washed with anhydrous ether. The crude peptide was dissolved in 10% aqueous acetic acid and filtered. The resin was washed with 10% aqueous acetic acid and the combined filtrates were collected and lyophilized to give crude peptide. The crude peptide was purified by counter-current distribution using n-butanol:acetic acid:water (4:1:5) as the partition phase to afford the pure peptide. The resulting polypeptide has the following sequence:

   V.

For identification, thin layer chromatography and electrophoresis were employed. The amino acid composition was determined using an amino acid analyzer.

Thin layer chromatography was performed on 20 μg samples on silica gel (Kieselgel, 5×20 cm) using 1:1:1:1 n-butanol:acetic acid:ethyl acetate:water as the solvent system ($R_f^1$) and on cellulose 6064 (Eastman 20×20 cm) using 15:10:3:12 n-butanol:pyridine:acetic acid:water as the solvent system ($R_f^2$). The $R_f$ values relative to H-ARG-LYS-ASP-VAL-TYR-OH were $R_f^1 = 1.84$ and $R_f^2 = 1.11$. Ninhydrin was used as a spray reagent.

Electrophoresis was performed on a 100 μg sample on Whitman No. 3 paper (5.7×55 cm) using a pH 5.6 pyridine-acetate buffer at a voltage of 1000 V for 1.0 hours. The pentapeptide had a mobility of 0.29 toward the cathode relative to H-ARG-LYS-ASP-VAL-TYR-OH. Ninhydrin and Pauly spray reagents were used.

EXAMPLE II

To determine the activity and characteristics of the polypeptide of Example I, determinations were carried out on healthy 5-6 week nu/nu mice of both sexes, the mice being bred on a BALB/c background (thymocytes expressing Thy-1.2 surface antigen) and maintained under conventional conditions. For the antisera, anti Thy-1.2 sera were prepared in Thy-1 congenic mice.

For the induction in vitro of Thy-1+ T cells or CR+ B cell differentiation, the induction of thymocyte differentiation from prothymocytes in vitro was performed as described in Komuro and Boyse, (Lancet, 1, 740, 1973), using the acquisition of Thy-1.2 as a marker of T cell differentiation. The induction of CR+ B cell differentiation from CR− B cell precursors in vitro was performed under similar conditions using as the assay criterion, the capacity of CR+ B cells to bind sheep erythrocytes coated with subagglutinating quantities of rabbit antibody and nonlytic complement. Spleen cell populations from healthy nu/nu mice fractionated on discontinuous bovine serum albumin gradients were used as the source of both precursor types (Thy-1− and CR−) because they have few or no Thy-1+ cells and low numbers of CR+ cells.

As a result of this determination it was found that the polypeptide displayed a selectivity of actions similar to that of Thymopoietin II in inducing the differentiation of T-lymphocytes but not of complement receptors (CR+) B-lymphocytes. The pentapeptide induced differentiation of Thy-1+ T cells in concentrations ranging from 1 pg to 10 ng/ml. It did not induce the differentiation of CR+ B cells in the same concentrations.

EXAMPLE III

Following the procedure of Example I, but substituting for the sarcosine used therein an equivalent amount of appropriately protected D-alanine, there is prepared the following pentapeptide: H-ARG-D-ALA-ASP-VAL-TYR-OH. This pentapeptide displays the same biological activity as the pentapeptide prepared in Example I.

EXAMPLE IV

Following the procedure of Example I using equivalent amounts of the appropriate amino acids (suitably protected) there are prepared the following pentapeptides (benzhydrylamine resin used to prepare "B"):
A. H-ARG-SAR-ASP-SAR-TYR-OH
B. H-ARG-SAR-ASP-SAR-TYR-NH$_2$
C. H-ARG-LYS-ASP-SAR-TYR-OH These pentapeptides display the same biological activity as the pentapeptide prepared in Example I.

The sequence of these peptides was determined by an amino acid analyzer. Thin layer chromatography and electrophoresis of B and C under the same conditions as for Example I yielded the following information.

| Peptide | $R_f^1$ | $R_f^2$ | Mobility toward cathode |
|---------|---------|---------|-------------------------|
| B       | 1.76    | 0.95    | 1.03                    |
| C       | 0.80    | 0.78    | 0.97                    |

EXAMPLE V

The protected pentapeptide resins prepared as in Examples I and III are each amidated (cleaved) by reaction with anhydrous ammonia by known methods, followed by deprotection and purification to prepare the following pentapeptide amides:
A. H-ARG-SAR-ASP-VAL-TYR-NH$_2$
B. H-ARG-D-ALA-ASP-VAL-TYR-NH$_2$

EXAMPLE VI

The peptides prepared in Examples I, III, and IVA are esterified to produce the ethyl alcohol derivatives. In preparation of this ester it is necessary to block the acid group on aspartic acid with a mild acid sensitive blocking group during preparation, with the preferred blocking group being t-butyl. The α-amino blocking group is sensitive to mild base, and is preferably fluorenylmethoxycarbonyl. Using such an α-amino blocking group, it may be removed for the addition of each amino acid residue without disturbing the acid-sensitive protecting group on the aspartic acid residue. After preparation of the protected pentapeptide resin, treatment with mild base followed by treatment with mild acid will remove these two protecting groups. Transesterification with ethyl formate using sulfuryl chloride as a catalyst will cleave the pentapeptide from the resin to selectively form the C-terminal ester. Esterification will not occur at the free acid of the aspartic acid residue. The remaining protective groups are removed and the peptide of the following formula is recovered:

A. H-ARG-SAR-ASP-VAL-TYR-OC$_2$H$_5$
B. H-ARG-D-ALA-ASP-VAL-TYR-OC$_2$H$_5$
C. H-ARG-SAR-ASP-SAR-TYR-OC$_2$H$_5$

EXAMPLE VII

Following the procedure of Example VI, but cleaving the peptide from the resin using methyl amine instead of ethyl formate and sulfuryl chloride, the following derivatives are formed and recovered:

A. H-ARG-SAR-ASP-VAL-TYR-NHCH$_3$
B. H-ARG-D-ALA-ASP-VAL-TYR-NHCH$_3$
C. H-ARG-SAR-ASP-SAR-TYR-NHCH$_3$

EXAMPLE VIII

Following the procedures of Examples I, III, and IVB, but substituting for the protected L-arginine used therein an equivalent amount of protected N-methyl arginine, there are prepared the substituted derivatives of the following formula:

A. CH$_3$-ARG-SAR-ASP-VAL-TYR-OH
B. CH$_3$-ARG-D-ALA-ASP-VAL-TYR-OH
C. CH$_3$-ARG-SAR-ASP-SAR-TYR-NH$_2$

EXAMPLE IX

Following the procedures of Examples I, III, and IVB, but substituting for the protected L-arginine used therein an equivalent amount of protected N-phenyl-L-arginine, there are prepared the phenyl substituted polypeptides of the following formula:

A. C$_6$H$_5$-ARG-SAR-ASP-VAL-TYR-OH
B. C$_6$H$_5$-ARG-D-ALA-ASP-VAL-TYR-OH
C. C$_6$H$_5$-ARG-SAR-ASP-SAR-TYR-NH$_2$

EXAMPLE X

Following the procedure of Example VI, but substituting equivalent amounts of the appropriately protected amino acids, there are produced the following:

A. CH$_3$-ARG-SAR-ASP-VAL-TYR-OC$_2$H$_5$
B. CH$_3$-ARG-D-ALA-ASP-VAL-TYR-OC$_2$H$_5$
C. H-ARG-SAR-ASP-SAR-TYR-OC$_2$H$_5$

EXAMPLE XI

Following the procedures of Example I, IVA, and IVB, but substituting for the protected L-arginine used therein an equivalent amount of suitably protected deaminoarginine, there are produced the following:

A. deamino-ARG-SAR-ASP-VAL-TYR-OH
B. deamino-ARG-SAR-ASP-SAR-TYR-OH
C. deamino-ARG-SAR-ASP-SAR-TYR-NH$_2$

EXAMPLES XII–XXI

Using the reaction techniques described hereinabove for the lengthening of the polypeptide chain, the following polypeptides are prepared which contain the active amino acid sequence but which are substituted on the terminal amino and carboxylic groups by R and R' to provide the polypeptides of the formula:

R-ARG-SAR-ASP-Y-TYR-R'  VI.

wherein Y is SAR or VAL and which is substituted by the amino acids given in the following Table as indicated.

| EXAMPLE NUMBER | R | R' |
|---|---|---|
| XII | GLN | OH |
| XIII | GLU-GLN | OH |
| XIV | GLY-GLU-GLN | OH |
| XV | GLY-GLU-GLN | VAL |
| XVI | GLY-GLU-GLN | VAL-GLN |
| XVII | GLY-GLU-GLN | VAL-GLN-LEU |
| XVIII | GLY-GLU-GLN | VAL-GLN-LEU-TYR |
| XIX | GLN | VAL |
| XX | GLN | VAL-GLN |
| XXI | GLN | VAL-GLN-LEU |

The polypeptide derivatives prepared in Examples V–XXI retain the biological activity as described herein for the unsubstituted pentapeptide of Formula I.

EXAMPLE XXII

Following the procedure of Example I using equivalent amounts of the appropriate amino acids (suitably protected) there are prepared the following pentapeptides (benzhydrylamine resin used to prepare peptide amides):

H-ARG-ALA-ASP-VAL-TYR-OH
H-ARG-LYS-GLU-VAL-TYR-OH
deamino-ARG-D-LYS-ASP-VAL-TYR-OH
H-ARG-SAR-GLU-SAR-TYR-NH$_2$
H-ARG-LYS-ASP-LEU-TYR-OH
H-ARG-LYS-ASP-ILE-TYR-OH

EXAMPLE XXIII

Peptides having decarboxy-TYR or

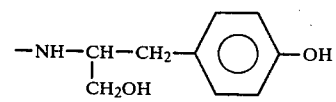

as the C-terminal amino acid residue are prepared following the procedure of Kirby and Warme described above. Using suitable amounts of the appropriate amino acids and amino acid derivatives (all suitably protected) there are prepared the following:

H—ARG—SAR—GLU—SAR—(decarboxy-TYR)

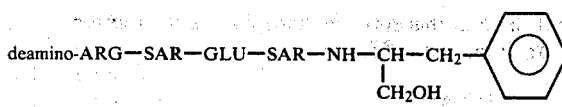

H-ARG-SAR-ASP-VAL-(decarboxy-TYR)

The peptides and derivatives prepared in Examples XXII and XXIII exhibit the same biological activity as the pentapeptide prepared in Example I.

The invention has been described herein with reference to certain preferred embodiments. However, as obvious variations will appear to those skilled in the art, the invention is not to be considered as limited thereto.

What is claimed is:

1. A peptide having the biological capability of inducing the differentiation of T-lymphocytes but not of complement receptor (CR+) B lymphocytes, said peptide having the following sequence:

A-X-Z-Y-B and the pharmaceutically acceptable salts thereof, wherein A is

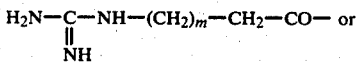

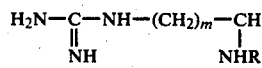

X is a suitable neutral, aliphatic or aromatic amino acid residue; e.g., one selected from the group consisting of ALA, 2-Me-ALA, GLY, LEU, ILE, LYS, THR, SER, PHE, MET, D-ALA, D-LEU, D-ILE, D-LYS, D-THR, allo-THR, D-SER, D-PHE, D-MET, and SAR; Z is

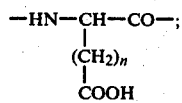

Y is GLY, SER, THR, LEU, ILE, VAL, or SAR; B is TYR-R', D-TYR-R', decarboxy-TYR, or

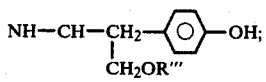

m is 3 or 4; n is 1, 2, or 3; R''' is hydrogen, $C_1$-$C_7$ alkyl, $C_6$-$C_{12}$ aryl, or $C_1$-$C_7$ alkanoyl; R and R' are terminal groups on said peptide which do not substantially affect the biological capability thereof, said R and R' being selected from the groups consisting of:

| R | R' |
|---|---|
| Hydrogen | OH |
| $C_1$-$C_7$ alkyl | $NH_2$ |
| $C_6$-$C_{12}$ aryl | NHR'' |
| $C_6$-$C_{20}$ alkaryl | N(R'')$_2$ |
| $C_6$-$C_{20}$ aralkyl | OR'' |
| $C_1$-$C_7$ alkanoyl | — |
| $C_2$-$C_7$ alkenyl | VAL |
| $C_2$-$C_7$ alkynyl | GLN |
| GLN | LEU |
| GLU | TYR |

| R | R' |
|---|---|
| GLY | VAL—GLN |
| GLU—GLN | VAL—LEU |
| GLY—GLN | VAL—TYR |
| GLY—GLU | GLN—LEU |
| GLY—GLU—GLN | GLN—TYR |
| | GLN—VAL |
| | LEU—TYR |
| | LEU—LEU |
| | TYR—LEU |
| | VAL—GLN—LEU |
| | VAL—GLN—LEU—TYR |
| | VAL—GLN—LEU—TYR—LEU | wherein R'' is $C_1$-$C_7$ alkyl, $C_2$-$C_7$ alkenyl, $C_2$-$C_7$ alkynyl, $C_6$-$C_{20}$ aryl, $C_6$-$C_{20}$ aralkyl, or $C_6$-$C_{20}$ alkaryl; provided that R-ARG-LYS-ASP-VAL-TYR-R' is excluded.

2. The peptide of claim 1 wherein m is 3 and n is 1 or 2.

3. The peptide of claim 2 wherein Z is ASP and Y is VAL or SAR.

4. The peptide of claim 3 wherein A is R-ARG and B is TYR-R'.

5. The peptide of claim 4 wherein X is SAR if Y is SAR.

6. A peptide according to claim 4 wherein R is hydrogen and R' is OH.

7. A peptide according to claim 4 wherein R is $CH_3CO$— and R' is OH.

8. A peptide according to claim 4 wherein R is $CH_3$ and R' is OH.

9. A peptide according to claim 4 wherein R is H and R' is —$NH_2$.

10. A peptide according to claim 4 wherein R is H and R' is —$NH(CH_3)$.

11. A peptide according to claim 4 wherein R is H and R' is —$N(C_2H_5)_2$.

12. A peptide according to claim 4 wherein R is $CH_3CO$— and R' is $NH_2$.

13. A peptide according to claim 4 wherein R is H and R' is —$OCH_3$.

14. A peptide according to claim 4 wherein R is H and R' is $OC_2H_5$.

15. A peptide according to claim 4 wherein R is phenyl and R' is —OH.

16. A peptide according to claim 4 wherein R is benzyl and R' is —OH.

17. A peptide according to claim 4 wherein R is tolyl- and R' is —OH.

18. A peptide according to claim 4 wherein R is GLN and R' is —OH.

19. A peptide according to claim 4 wherein R is GLU and R' is —OH.

20. A peptide according to claim 4 wherein R is GLY and R' is —OH.

21. A peptide according to claim 4 wherein R is H and R' is VAL.

22. A peptide according to claim 4 wherein R is H and R' is GLN.

23. A peptide according to claim 4 wherein R is H and R' is LEU.

24. A peptide according to claim 4 wherein R is H and R' is TYR.

25. A peptide according to claim 4 wherein R is H and R' is VAL-GLN.

26. A peptide according to claim 4 wherein R is GLN and R' is VAL.

27. A peptide according to claim 4 wherein R is GLU-GLN and R' is VAL-GLN.

28. A pentapeptide of the following sequence:

H-ARG-SAR-ASP-VAL-TYR-NH₂ and the pharmaceutically acceptable salts thereof.

29. A pentapeptide of the following sequence:

H-ARG-D-ALA-ASP-VAL-TYR-NH₂ and the pharmaceutically acceptable salts thereof.

30. A pentapeptide of the following sequence:

H-ARG-SAR-ASP-SAR-TYR-NH₂ and the pharmaceutically acceptable salts thereof.

31. A peptide of formula:

A-SAR-ASP-Y-B wherein A is deamino ARG or H-ARG; Y is VAL or SAR; B is decarboxy-TYR, TYR-R', or

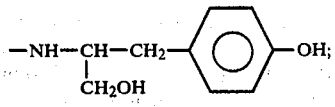

and R' is H, OH, or NH₂; and the pharmaceutically acceptable salts thereof.

32. The peptide of claim 31 wherein Y is SAR.

33. The peptide of claim 32 wherein B is TYR-NH₂.

* * * * *